United States Patent
Akiya et al.

(10) Patent No.: US 10,981,857 B2
(45) Date of Patent: Apr. 20, 2021

(54) METHOD FOR PRODUCING α-FLUORO ACRYLIC ACID ESTER, AND COMPOSITION CONTAINING HIGHLY-PURE FLUOROCYCLOPROPANE DERIVATIVE, AND COMPOSITION CONTAINING HIGHLY-PURE α-FLUORO ACRYLIC ACID ESTER

(71) Applicant: AGC INC., Chiyoda-ku (JP)

(72) Inventors: Takashi Akiya, Chiyoda-ku (JP); Mitsugu Kasagawa, Chiyoda-ku (JP); Naoki Ichinokawa, Chiyoda-ku (JP); Yu Onozaki, Chiyoda-ku (JP); Satoshi Kawaguchi, Chiyoda-ku (JP); Yusuke Tomiyori, Chiyoda-ku (JP); Arata Yasuda, Chiyoda-ku (JP)

(73) Assignee: AGC INC., Chiyoda-ku (JP)

( * ) Notice: Subject to any disclaimer, the term of this patent is extended or adjusted under 35 U.S.C. 154(b) by 0 days.

(21) Appl. No.: 16/087,369

(22) PCT Filed: Feb. 24, 2017

(86) PCT No.: PCT/JP2017/007116
§ 371 (c)(1),
(2) Date: Sep. 21, 2018

(87) PCT Pub. No.: WO2017/163756
PCT Pub. Date: Sep. 28, 2017

(65) Prior Publication Data
US 2019/0263746 A1 Aug. 29, 2019

(30) Foreign Application Priority Data

Mar. 23, 2016 (JP) .............................. JP2016-059110
Mar. 23, 2016 (JP) .............................. JP2016-059111
Mar. 23, 2016 (JP) .............................. JP2016-059112

(51) Int. Cl.
| | | |
|---|---|---|
| *C07C 43/313* | (2006.01) | |
| *C07C 67/00* | (2006.01) | |
| *C07C 67/62* | (2006.01) | |
| *C07C 69/653* | (2006.01) | |
| *C07C 41/48* | (2006.01) | |

(52) U.S. Cl.
CPC .............. *C07C 67/62* (2013.01); *C07C 41/48* (2013.01); *C07C 43/313* (2013.01); *C07C 67/00* (2013.01); *C07C 69/653* (2013.01)

(58) Field of Classification Search
CPC ......... C07C 41/48; C07C 41/50; C07C 41/54; C07C 41/58; C07C 43/188; C07C 43/192; C07C 43/303; C07C 43/505; C07C 43/313; C07C 67/00; C07C 67/317; C07C 67/327; C07C 67/54; C07C 67/62; C07C 69/653

See application file for complete search history.

(56) References Cited

U.S. PATENT DOCUMENTS

| 3,646,165 A | 2/1972 | Billere et al. |
| 4,570,018 A * | 2/1986 | Aoki ..................... C07C 43/192 558/250 |
| 6,096,795 A | 8/2000 | Abusleme et al. |
| 2010/0160552 A1 | 6/2010 | Larichev |
| 2017/0057902 A1 | 3/2017 | Yasuda et al. |

FOREIGN PATENT DOCUMENTS

| CN | 105130798 A * | 12/2015 |
| CN | 105130798 A | 12/2015 |

(Continued)

OTHER PUBLICATIONS

International Search Report dated May 23, 2017 in PCT/JP2017/007116 filed Feb. 24, 2017.

(Continued)

*Primary Examiner* — Matthew R Diaz
(74) *Attorney, Agent, or Firm* — Oblon, McClelland, Maier & Neustadt, L.L.P.

(57) ABSTRACT

The present invention provides a production method of α-fluoroacrylate ester, a composition containing a highly-pure fluorocyclopropane derivative and a composition containing highly-pure α-fluoroacrylate ester. The present invention relates to a method of producing a compound represented by the following formula (F), including subjecting a composition containing a compound represented by the following formula (A) to a purification treatment in the order of distillation and washing with an aqueous alkali solution to give a purified product containing a compound represented by the following formula (A), and subjecting the purified product to a thermal decomposition reaction, a composition containing a highly-pure compound represented by the following formula (A), and a composition containing a highly-pure compound represented by the following formula (F), wherein R may be the same or different and is a monovalent hydrocarbon group, and X is a halogen atom:

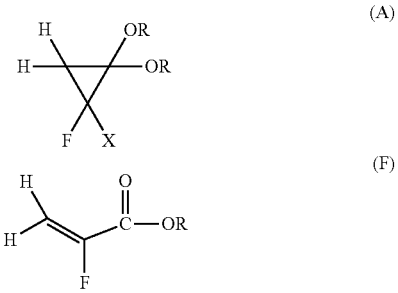

13 Claims, No Drawings

FOREIGN PATENT DOCUMENTS

| | | | |
|---|---|---|---|
| CN | 106397206 A | * | 2/2017 |
| CN | 106397206 A | | 2/2017 |
| FR | 2 573 069 A1 | | 5/1986 |
| JP | 48-32190 B1 | | 10/1973 |
| JP | 59-222430 A | | 12/1984 |
| JP | 7-188337 A | | 7/1995 |
| JP | 2012-513531 A | | 6/2012 |
| WO | WO 2017/033955 A1 | | 3/2017 |

OTHER PUBLICATIONS

Yasuhiro Nishitani, et al., "cis-Halovinylthioacetamido side chain, a new effective structural element for 7β-substitution in cephem and oxacephem antibiotics II. 7β-cis-Fluorovinylthioacetamino-7α-methoxy-1-oxacephems" The Journal of Antibiotics, vol. XLI, No. 3, Mar. 1988, pp. 332-342.

* cited by examiner

METHOD FOR PRODUCING α-FLUORO ACRYLIC ACID ESTER, AND COMPOSITION CONTAINING HIGHLY-PURE FLUOROCYCLOPROPANE DERIVATIVE, AND COMPOSITION CONTAINING HIGHLY-PURE α-FLUORO ACRYLIC ACID ESTER

TECHNICAL FIELD

The present invention relates to a production method of α-fluoroacrylate ester, a composition containing a highly-pure fluorocyclopropane derivative and a composition containing highly-pure α-fluoroacrylate ester.

BACKGROUND ART

α-Fluoroacrylate ester is useful as a monomer for polymers used for optical material, paint, resist material and the like.

Patent document 1 describes a production method of ethyl α-fluoroacrylate, which includes converting an ethylene derivative obtained from potassium t-butoxide and a large excess of chlorofluorocarbon to a fluorocyclopropane derivative and then decomposing same.

Patent document 2 describes a production method of methyl α-fluoroacrylate, which includes purifying a reaction product (organic layer) of $CH_2=C(OCH_3)_2$ and $CHCl_2F$ by washing with an aqueous potassium hydroxide solution and then distilling the reaction product and subjecting the obtained 1-chloro-1-fluoro-2,2-dimethoxycyclopropane to a thermal decomposition reaction.

DOCUMENT LIST

Patent Documents

Patent document 1: European patent application publication No. 0127920
Patent document 2: Chinese patent application publication No. 105130798

SUMMARY OF THE INVENTION

Problems to be Solved by the Invention

According to the study of the present inventors, 1-chloro-1-fluoro-2,2-dimethoxycyclopropane obtained by any of the production methods described in the patent documents had low purity, and highly-pure methyl α-fluoroacrylate was not obtained efficiently by using same. In addition, methyl α-fluoroacrylate has low preservation stability and is readily decomposed with the lapse of time or easily polymerized to form a homopolymer.

The problem of the present invention is to provide a production method of α-fluoroacrylate ester. In addition, the present invention aims to provide a composition containing a highly-pure fluorocyclopropane derivative preferably used for the production of α-fluoroacrylate ester, and a composition containing highly-pure α-fluoroacrylate ester preferably used as a monomer for various polymers. Furthermore, the present invention also aims to provide a method for storing α-fluoroacrylate ester stably for a long term.

Means of Solving the Problems

The present inventors have conducted intensive studies in an attempt to solve the aforementioned problems and found that the above-mentioned problems can be by solved by the following constitution.

Therefore, the present invention provides the following.
[1] A method of producing a compound represented by the following formula (F), comprising subjecting a composition comprising a compound represented by the following formula (A) to a purification treatment in the order of distillation and washing with an aqueous alkali solution to give a purified product comprising a compound represented by the following formula (A), and subjecting the purified product to a thermal decomposition reaction to give a compound represented by the following formula (F):

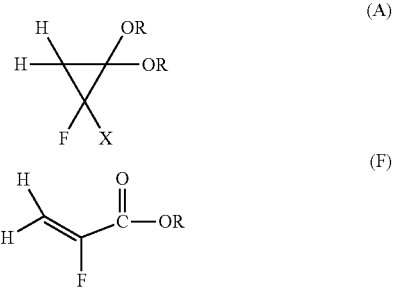

wherein each R may be the same or different and is a monovalent hydrocarbon group, and X is a halogen atom.
[2] The production method of the above-mentioned [1], wherein the aforementioned composition is obtained by reacting a compound represented by the formula $CH_2=C(OR)_2$ (wherein each symbol is as defined above) and a compound represented by the formula $CHClFX$ (wherein each symbol is as defined above) in the presence of alkali metal hydroxide.
[3] The production method of the above-mentioned [1] or [2], wherein the aforementioned distillation comprises evaporating under reduced pressure at 70° C. or lower.
[4] The production method of any of the above-mentioned [1] to [3], wherein an alkali concentration of the aqueous alkali solution is maintained at 40 mass % or less in the aforementioned washing.
[5] A method for storing a compound represented by the aforementioned formula (F), comprising obtaining a compound represented by the aforementioned formula (F) by the production method of any of the above-mentioned [1] to [4], and retaining the compound in a state containing an aliphatic hydrocarbon of more than 0 ppm and not more than 50000 ppm relative to the compound.
[6] A method for storing a compound represented by the aforementioned formula (F), comprising obtaining a compound represented by the aforementioned formula (F) by the production method of any of the above-mentioned [1] to [4] and retaining the compound at pH 6.5 or below.
[7] A method for storing a compound represented by the aforementioned formula (F), comprising obtaining a compound represented by the aforementioned formula (F) by the production method of any of the above-mentioned [1] to [4] and retaining the compound in a state containing a hydrogen halide of more than 0 ppm and not more than 10000 ppm relative to the compound.
[8] A composition comprising a compound represented by the following formula (A) and one or more kinds of compounds selected from a compound represented by the following formula (P) and a compound represented by the following formula (Q), wherein a content of the compound represented by the following formula (A) is not less than 80.0 mol % and the total content of the one or more kinds of compounds is not more than 1.00 mol % relative to the compound represented by the following formula (A):

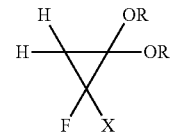
(A)

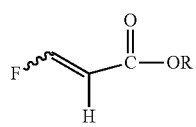
(P)

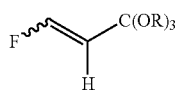
(Q)

wherein each R may be the same or different and is a monovalent hydrocarbon group, and a wavy line shows that a steric configuration relating to a double bond of the fluorine atom may be E or Z.

[9] A composition comprising a compound represented by the following formula (A) and a compound represented by the following formula (P), wherein a content of the compound represented by the following formula (A) is not less than 80.0 mol % and a content of the compound represented by the following formula (P) is not more than 0.35 mol % relative to the compound represented by the following formula (A):

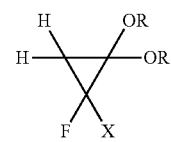
(A)

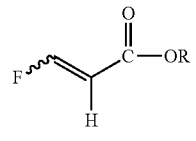
(P)

wherein each R may be the same or different and is a monovalent hydrocarbon group, and a wavy line shows that a steric configuration relating to a double bond of the fluorine atom may be E or Z.

[10] A composition comprising a compound represented by the following formula (F) and one or more kinds of compounds selected from a compound represented by the following formula (P) and a compound represented by the following formula (Q), wherein a content of the compound represented by the following formula (F) is not less than 95.0 mol % and the total content of the one or more kinds of compounds is not more than 0.30 mol % relative to the compound represented by the following formula (F):

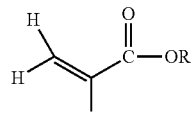
(F)

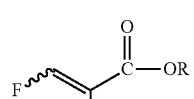
(P)

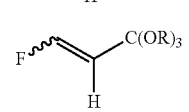
(Q)

wherein each R may be the same or different and is a monovalent hydrocarbon group, and a wavy line shows that a steric configuration relating to a double bond of the fluorine atom may be E or Z.

[11] The composition of the above-mentioned [10] further comprising aliphatic hydrocarbon at a content of more than 0 ppm and not more than 50000 ppm relative to the compound represented by the aforementioned formula (F).

[12] The composition of the above-mentioned [10] further comprising hydrogen halide at a content of more than 0 ppm and not more than 10000 ppm relative to the compound represented by the aforementioned formula (F).

[13] A composition comprising a compound represented by the following formula (F) and a compound represented by the following formula (P), wherein a content of the compound represented by the following formula (F) is not less than 95.0 mol % and a content of the compound represented by the following formula (P) is not more than 0.20 mol % relative to the compound represented by the following formula (F):

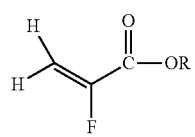
(F)

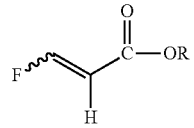
(P)

wherein each R may be the same or different and is a monovalent hydrocarbon group, and a wavy line shows that a steric configuration relating to a double bond of the fluorine atom may be E or Z.

[14] The composition of the above-mentioned [13] further comprising aliphatic hydrocarbon at a content of more than 0 ppm and not more than 50000 ppm relative to the compound represented by the aforementioned formula (F).

[15] The composition of the above-mentioned [13] further comprising hydrogen halide at a content of more than 0 ppm and not more than 10000 ppm relative to the compound represented by the aforementioned formula (F).

Effect of the Invention

According to the present invention, a composition containing highly-pure fluorocyclopropane can be produced with high efficiency. Using the composition, a composition containing highly-pure α-fluoroacrylate ester can be produced with high efficiency. According to the present invention, moreover, the highly-pure α-fluoroacrylate ester obtained by the present invention is superior in polymerizability. Thus, a polymer having superior property can easily be obtained by homopolymerization and copolymerization with other monomer. A polymer obtained from the composition containing highly-pure α-fluoroacrylate ester of the present invention can exhibit high function as an optical material, paint, semiconductor resist material or the like.

DESCRIPTION OF EMBODIMENTS

The terms in the present specification are defined as follows.

A numerical range expressed using "-" means a range including the numerical values indicated before and after "-" as the lower limit value and the upper limit value.

The "halogen atom" is a fluorine atom, a chlorine atom, a bromine atom or an iodine atom.

The "monovalent hydrocarbon group" is a group in which one hydrogen atom is removed from a carbon atom of a hydrocarbon. An etheric oxygen atom may be contained between carbon atom-carbon atom bonds in the monovalent hydrocarbon group. The hydrogen atom of the carbon atom-hydrogen atom bond of the monovalent hydrocarbon group may be substituted with a halogen atom. The number of carbon atoms of the monovalent hydrocarbon group is preferably 1-20.

The present invention relates to a production method of a compound represented by the following formula (F) (hereinafter to be also indicated as compound (F)) which is α-fluoroacrylate ester, a composition containing a compound represented by the following formula (A) (hereinafter to be also indicated as compound (A)) which is a fluorocyclopropane derivative, and a composition containing compound (F):

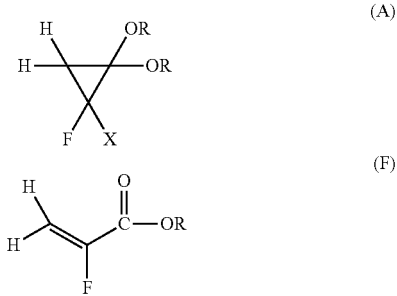

In the formulas, each R is a monovalent hydrocarbon group, and X is a halogen atom. When R is present in plurality in the formulas, each R may be the same or different and is preferably the same from the aspect of easy availability.

R is preferably an alkyl group, an aralkyl group or an aryl group, each having a carbon number of 1-20, more preferably an alkyl group with a carbon number of 1-20, particularly preferably a methyl group, an ethyl group, an n-propyl group, an iso-propyl group or a tert-butyl group, and most preferably a methyl group. When two R in compound (A) are methyl groups, the temperature of the below-mentioned distillation is adjusted with ease and highly-pure compound (A) is more efficiently produced.

X is preferably a chlorine atom or a fluorine atom, particularly preferably a chlorine atom.

Specific examples of compound (A) include the following compounds.

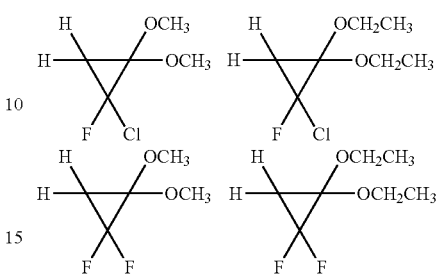

Specific examples of compound (F) include the following compounds.

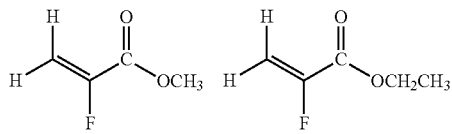 [SMILES: C=C(F)C(=O)OC ; C=C(F)C(=O)OCC]

The present invention provides a production method of compound (F), comprising subjecting a composition containing compound (A) to a purification treatment in the order of distillation and washing with an aqueous alkali solution to give a purified product containing compound (A), and subjecting the purified product to a thermal decomposition reaction.

The composition containing compound (A) in the present invention is preferably a composition obtained by reacting a compound represented by the formula $CH_2=C(OR)_2$ (hereinafter to be also indicated as compound (B)) and a compound represented by the formula CHClFX (hereinafter to be also indicated as halomethane) in the presence of alkali metal hydroxide (definitions and preferable ranges of R and X in the formulas are as mentioned above). In the following, the above-mentioned reaction is also indicated as reaction (1) and the composition obtained by reaction (1) is also indicated as composition (1).

Specific examples of compound (B) include $CH_2=C(OCH_3)_2$, $CH_2=C(OCH_2CH_3)_2$, $CH_2=C(OCH_2CH_2CH_3)_2$, $CH_2=C(OCH_2CH_2CH_2CH_3)_2$, $CH_2=C(OCH(CH_3)CH_2CH_3)_2$, $CH_2=C(OCH(CH_3)_2)_2$, and $CH_2=C(OC(CH_3)_3)_2$.

Examples of the production method of compound (B) include a method including contacting a compound represented by the formula $CH_3-C(OR)_3$ (wherein definition and preferable range of R are as mentioned above) with a solid catalyst in the gaseous phase to cause a de R—OH reaction.

Specific examples of halomethane include $CHCl_2F$ and $CHClF_2$.

The amount of halomethane to be used relative to compound (B) in reaction (1) is preferably not less than 1-fold mol, more preferably 1-5-fold mol, particularly preferably 1-2-fold mol.

The alkali metal hydroxide in reaction (1) is a compound promoting a reaction to generate carbene from halomethane, and is particularly preferably potassium hydroxide or sodium hydroxide. The amount thereof to be used is preferably 1-10-fold mol, preferably 1-8-fold mol, more preferably 1-6-fold mol, relative to halomethane.

Reaction (1) is preferably performed further in the presence of a solvent.

The solvent is preferably water, aliphatic hydrocarbon, halogenated aliphatic hydrocarbon, aromatic hydrocarbon, or halogenated aromatic hydrocarbon. Specific examples of the solvent include benzene, toluene, xylene, monochlorobenzene, dichlorobenzene, trichlorobenzene, petroleum ether, pentane, hexane, cyclohexane, heptane, octane, nonane, decane, undecane, dodecane, tridecane, tetradecane, dichloromethane, chloroform and carbon tetrachloride, and petroleum ether, pentane, hexane, cyclohexane, heptane, octane, nonane, decane, undecane, dodecane, tridecane or tetradecane is particularly preferable. Only one kind of solvent may be used or two or more kinds thereof may be used in combination.

The amount of the solvent is preferably 10-1000 volume %, more preferably 50-800 volume %, per 100 volume % of compound (B).

Reaction (1) is preferably performed further in the presence of a phase-transfer catalyst. The phase-transfer catalyst is preferably a quaternary ammonium salt, and preferably tetrabutylammonium bromide or tetrabutylammonium chloride. The phase-transfer catalyst may also be used as a catalyst between two kinds of solvent layers under phase separation.

Reaction (1) is generally performed by charging a solvent, alkali metal hydroxide and a phase-transfer catalyst in a reactor, and then sequentially or continuously adding compound (B) and halomethane thereto.

The reaction temperature in the reaction (1) is preferably −20° C. to +50° C., more preferably −10° C. to +40° C., particularly preferably 0° C. to +30° C.

The reaction pressure in reaction (1) is not particularly limited.

The resultant product directly obtained in reaction (1) includes a reaction product of alkali metal hydroxide and halomethane (e.g., the reaction product is KCl when the alkali metal hydroxide is potassium hydroxide and halomethane is $CHCl_2F$, and KF when the former is potassium hydroxide and the latter is $CHClF_2$). Composition (1) is preferably a composition after removal of the reaction product. The removal is generally performed by filtration or a partitioning operation of the reaction product.

Generally, a composition containing compound (A), for example, composition (1), contains as impurity one or more kinds of compounds selected from a compound represented by the following formula (P) (hereinafter to be also indicated as compound (P)) and a compound represented by the following formula (Q) (hereinafter to be also indicated as compound (Q)) (wherein the definition and preferable range of R are as mentioned above, and a wavy line shows that a steric configuration relating to a double bond of the fluorine atom may be E or Z).

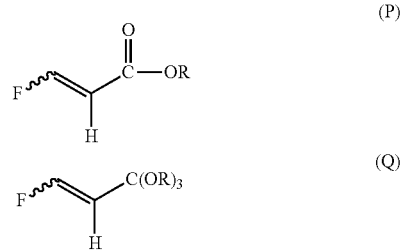

Compound (P) and compound (Q) have properties (boiling point, polarity) approximate to those of the below-mentioned compound (F). A composition containing compound (A) such as composition (1) and the like generally contains one or more kinds of compounds selected from compound (P) and compound (Q) at not less than 0.01 mol % relative to compound (A). In addition, composition (1) contains said one or more kinds of compounds at not more than 2 mol % relative to compound (A). In the present specification, "mol %" is regarded as an area percentage value (GC area %) of the detection peak of each compound, which is detected by a gas chromatography method (FID detector).

In the present specification, compound (P) is also regarded as a compound having a molecular weight of 104.1 by mass spectrometry, and a relative retention time of 0.63 when the retention time of compound (A) is 1 in an analysis by a gas chromatography method. In addition, compound (Q) is also regarded as a compound having a molecular weight of 150.2 by mass spectrometry, and a relative retention time of 1.02 when the retention time of compound (A) is 1 in an analysis by a gas chromatography method.

The detail of the distillation and washing with an aqueous alkali solution in the present invention is described below.

The holding range of the internal temperature of the system in the distillation is preferably not more than 70° C., particularly preferably not more than 50° C. The internal temperature of the system means the temperature of the entire system and generally means the internal temperature of the pot of the distillation column (bottom). The lower limit of the internal temperature of the system is appropriately determined from the boiling point of compound (A) and is generally 20° C. When the internal temperature of the system is maintained in the above-mentioned range, due to the decomposition of compound (A), by production of impurities such as compound (P), compound (Q) and the like is suppressed, and removal of impurities by the below-mentioned washing is facilitated.

Distillation may be any of pressurized distillation, atmospheric distillation and reduced pressure distillation, and is appropriately determined from the boiling point of compound (A). Reduced pressure distillation is preferable since reflux volume and reflux ratio are ensured.

A distillate of a composition containing compound (A) obtained by distillation may be directly washed or may be provided via other operations.

In the washing, it is preferable to contact an aqueous alkali solution and a distillate by stirring, and partition the mixture by standing still to give an organic layer that is a purified product containing compound (A). The organic layer may be further washed with water or dried. As a drying method, a method using a desiccant such as molecular sieve, zeolite, aluminum oxide, calcium chloride and the like can be mentioned.

In the washing, the holding range of the alkali concentration of an aqueous alkali solution is consistently preferably not more than 40 mass %, more preferably not more than 30 mass %, particularly preferably not more than 15 mass %. The lower limit of the holding range of an alkali concentration is preferably 1 mass %, particularly preferably 5 mass %. When the concentration is maintained in the above-mentioned range, the washing time can be shortened. In the washing, the volume ratio of the aqueous solution to the volume of the distillate is preferably 0.05-50 times. When the volume is maintained in the above-mentioned range, impurities are easily removed while suppressing decomposition of compound (A).

In the washing, the amount of alkali is preferably not less than 0.01-fold mol and not more than 1-fold mol, particularly preferably 0.03-0.5-fold mol, relative to compound (A).

The aqueous alkali solution is an aqueous solution of a basic compound. As the basic compound, hydroxides of alkaline earth metal or alkali metal such as sodium hydroxide, potassium hydroxide and the like, metal carbonates such as sodium carbonate, potassium carbonate and the like; and metal hydrogen phosphate salts or metal phosphates such as sodium phosphate, potassium phosphate, sodium hydrogen phosphate, potassium hydrogen phosphate and the like can be mentioned.

The basic compound is preferably alkali metal hydroxide or alkaline earth metal hydroxide, particularly preferably potassium hydroxide or sodium hydroxide. The basic compound may be used alone or two or more kinds thereof may be used in combination.

In the washing, the contact time of the distillate and the aqueous alkali solution is preferably not more than 600 min, preferably not more than 480 min, particularly preferably not more than 300 min. The lower limit is generally 10 min. In this case, impurities tend to be efficiently removed while suppressing decomposition of compound (A).

The purified product containing compound (A) in the present invention is highly-pure compound (A) obtained by subjecting a composition containing compound (A) to a purification treatment including distillation and washing with an aqueous alkali solution in this order. According to the study of the present inventors, when the purification treatment included washing with an aqueous alkali solution and distillation in this order, compound (P) and compound (Q), particularly compound (P), tended to be newly by-produced in the distillation, and highly-pure compound (A) could not be obtained.

That is, according to the production method of the present invention, a composition containing highly-pure compound (A), comprising compound (A) and one or more kinds of compounds selected from compound (P) and compound (Q), wherein the content of compound (A) is not less than 80.0 mol % and the total content of the one or more kinds of compounds is not more than 1.00 mol % relative to compound (A) (hereinafter to be also indicated as composition (A)) is obtained.

The content of compound (A) in composition (A) is preferably not less than 90.0 mol %, more preferably not less than 98.0 mol %, particularly preferably not less than 99.0 mol %. The upper limit amount thereof is less than 100.0 mol %.

The total content of one or more kinds of compounds in composition (A) is preferably not more than 0.75 mol %, particularly preferably not more than 0.50 mol %, relative to compound (A). The lower limit amount thereof is generally more than 0 mol %, specifically 0.01 mol %.

In another embodiment of composition (A), a composition containing compound (A) and compound (P), wherein the content of compound (A) is not less than 80.0 mol % and the content of compound (P) is not more than 0.35 mol % relative to compound (A) can also be mentioned.

The content of compound (A) in the composition is preferably not less than 90.0 mol %, more preferably not less than 98.0 mol %, particularly preferably not less than 99.0 mol %. The upper limit amount thereof is less than 100.0 mol %.

The content of compound (P) in the composition is preferably not more than 0.25 mol %, more preferably not more than 0.20 mol %, particularly preferably not more than 0.10 mol %, relative to compound (A). The lower limit amount thereof is generally more than 0 mol %, specifically 0.01 mol %.

As specific embodiments of compound (A), compound (P) and compound (Q) in composition (A), a compound represented by the following formula (A1) (hereinafter to be also indicated as compound (A1)), a compound represented by the following formula (P1) (hereinafter to be also indicated as compound (P1)) and a compound represented by the following formula (Q1) (hereinafter to be also indicated as compound (Q1)) can be mentioned. In the formulas, $R^1$ is the same and is a methyl group, an ethyl group, an n-propyl group, an iso-propyl group, an n-butyl group, an iso-butyl group or a tert-butyl group, preferably a methyl group. In the formulas, a wavy line shows that a steric configuration relating to a double bond of the fluorine atom may be E or Z.

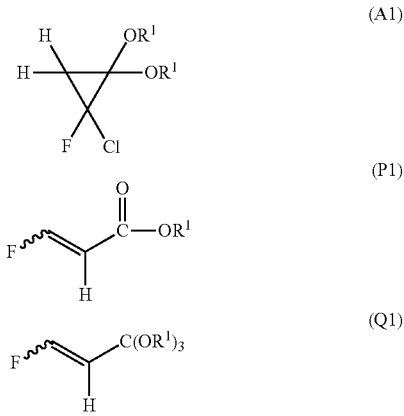

In the production method of the present invention, the obtained purified product containing compound (A) is subjected to a thermal decomposition reaction to give compound (F).

The thermal decomposition reaction can be carried out by heating. The thermal decomposition reaction may be a gaseous phase reaction or a liquid phase reaction. The temperature of the thermal decomposition reaction is preferably 80° C.-400° C., more preferably 100° C.-350° C., further preferably 120° C.-300° C. The pressure of the thermal decomposition reaction is not particularly limited.

When the thermal decomposition reaction is carried out by a liquid phase reaction, it is preferably performed in the presence of a solvent. The solvent only needs to be inert under the conditions of thermal decomposition reaction, and hydrocarbon solvents, aromatic hydrocarbon solvents, alcohol solvents, halogenated hydrocarbon solvents and halogenated aromatic hydrocarbon solvents can be mentioned, and a halogenated aromatic hydrocarbon solvent, an aromatic hydrocarbon solvent, or saturated aliphatic hydrocarbon in the below-mentioned first method for storing is preferable. The amount of the solvent to be used is preferably 0-1000 volume % relative to compound (A).

In addition, compound (F) produced by the thermal decomposition reaction is highly polymerizable, and the thermal decomposition reaction is preferably performed in the presence of a polymerization inhibitor. The amount of the polymerization inhibitor to be used is preferably not less than ppm, particularly preferably 20-50000 ppm, relative to compound (F) to be produced.

The production method of the present invention can directly obtain a composition containing highly-pure compound (F) by undergoing thermal decomposition reaction of the composition of highly-pure compound (A), which has a small content of compound (P) or compound (Q) having similar physical properties (boiling point, polarity) to those of compound (F) and hardly separated from compound (F).

According to the present invention, a composition containing highly-pure compound (F), comprising compound (F) and one or more kinds of compounds selected from compound (P) and compound (Q), wherein the content of compound (F) is not less than 95.0 mol % and the total content of the one or more kinds of compounds is not more than 0.30 mol % relative to compound (F) (hereinafter to be also indicated as composition (F)) is provided.

In composition (F) of the present invention, the content of compound (F) and the total content of the one or more kinds of compounds are each in the aforementioned ranges, the storage stability of the composition is superior, and the physical properties of a polymer obtained by polymerizing the composition are also superior.

On the other hand, when the content of compound (F) is less than 95.0 mol %, the properties (physical properties derived from compound (F) such as water-repellency and oil-repellency, low refractive index, transparency and the like) of a polymer obtained by polymerizing the composition tend to be degraded. When the composition does not contain the one or more kinds of compounds, the storage stability of the composition is easily deteriorated. Furthermore, when the total content of the one or more kinds of compounds is more than 0.30 mol %, the aforementioned degradation of the physical properties of the polymer, as well as polymerization easily discontinues during polymerization of the composition, and the polymerization property (molecular weight, molecular weight 2c distribution etc.) is difficult to control.

The content of compound (F) in composition (F) is preferably more than 98.5 mol %, particularly preferably not less than 99.0 mol %. The upper limit amount thereof is less than 100.0 mol %.

The total content of one or more kinds of compounds in composition (F) is preferably not more than 0.25 mol %, particularly preferably not more than 0.10 mol %, relative to compound (F). The lower limit amount thereof is generally more than 0 mol %, specifically 0.01 mol %.

In another embodiment of composition (F), a composition containing highly-pure compound (F), comprising compound (F) and compound (P), wherein the content of compound (F) is not less than 95.0 mol % and the content of compound (P) is not more than 0.20 mol % relative to compound (F) can be mentioned.

The content of compound (F) in the composition is preferably more than 98.5 mol %, particularly preferably not less than 99.0 mol %. The upper limit amount thereof is less than 100.0 mol %.

The content of compound (P) in the composition is preferably not more than 0.10 mol %, particularly preferably not more than 0.05 mol %, relative to compound (F). The lower limit amount thereof is generally more than 0 mol %, specifically 0.01 mol %.

Specific embodiments of compound (P) and compound (Q) in composition (F) are a compound represented by the following formula (F1) (wherein definition and preferable range of $R^1$ are as mentioned above), compound (P1) and compound (Q1).

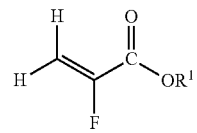

According to the present invention, a production method of a polymer including polymerizing compound (F) obtained by the production method of the present invention or the composition (F) of the present invention to obtain a polymer is also provided.

The polymerization may be homopolymerization of compound (F) obtained by the production method of the present invention or the composition (F) of the present invention, or copolymerization with other monomer.

The polymerization conditions such as polymerization type, temperature, pressure and the like, are not particularly limited.

As a preferable embodiment of polymerization, embodiments described in JP-A 2012-500806, JP-A 2013-522448 and the like can be mentioned. More specifically, an embodiment including copolymerizing compound (F) obtained by the production method of the present invention or the composition (F) of the present invention, divinylbenzene and alkadiene in water by the action of a radical polymerization initiator can be mentioned.

As described above, compound (F) obtained by the production method of the present invention or the composition (F) of the present invention is superior in polymerizability. Thus, even when subjected to copolymerization in which crosslinking between polymers also proceeds with crosslinkable monomers such as divinylbenzene, alkadiene and the like, or copolymerization with poorly polymerizable monomers such as alkadiene and the like, a polymer superior in the desired physical property can be formed easily.

Compound (F) obtained by the production method of the present invention or the composition (F) of the present invention is preferably stored in a more stable state until it is provided for use.

As a first method for storing compound (F), a method for storing compound (F) while retaining an aliphatic hydrocarbon at more than 0 ppm and not more than 50000 ppm relative to compound (F) can be mentioned. That is, compound (F) can be stably stored for a long term in a state of a composition containing compound (F) and aliphatic hydrocarbon wherein aliphatic hydrocarbon is contained at more than 0 ppm and not more than 50000 ppm relative to compound (F). A preferable embodiment of such composition is a composition containing composition (F) of the present invention and hydrogen halide wherein aliphatic hydrocarbon is contained at more than 0 ppm and not more than 50000 ppm relative to compound (F) can be mentioned.

Aliphatic hydrocarbon means chain or cyclic non-aromatic hydrocarbon. Aliphatic hydrocarbon only needs to be compatible with compound (F), and may be a saturated aliphatic hydrocarbon or an unsaturated aliphatic hydrocarbon.

Examples of the saturated aliphatic hydrocarbon include alkane having a chain structure (e.g., pentane, hexane, octane, nonane, decane, undecane, dodecane, tridecane, tetradecane, pentadecane, hexadecane), and cycloalkane having a cyclic structure (e.g., cyclopropane, cyclobutane, cyclopentane, cyclohexane, cyclodecane).

Examples of the unsaturated aliphatic hydrocarbon include alkene having a chain structure having one double bond (e.g., ethylene, propylene, butene, pentene, hexene, octene, decene, dodecene, tetradecene, hexadecene), cycloalkene having a cyclic structure having one double bond (e.g., cyclobutene, cyclopropene, cyclopentene, cyclohexene, cyclooctene), and alkyne having a chain structure having one triple bond (e.g., acetylene, propyne, butyne, pentyne, hexyne, octyne, nonyne, decyne).

The carbon number of the aliphatic hydrocarbon is preferably 4-12, particularly preferably 5-8.

As the aliphatic hydrocarbon, saturated aliphatic hydrocarbon is preferable, saturated aliphatic hydrocarbon having a carbon number of 4-12 is preferable, pentane, hexane, octane, nonane, decane, cyclopentane, cyclohexane or cyclodecane is particularly preferable, and hexane is most preferable. In the present invention, aliphatic hydrocarbon may be used alone or two or more kinds thereof may be used in combination.

The lower limit value of the amount of aliphatic hydrocarbon is more than 0 ppm, preferably 10 ppm, particularly preferably 100 ppm, per 1 g of compound (F). The upper limit value is 50000 ppm, preferably 30000 ppm, particularly preferably 20000 ppm. When the amount of aliphatic hydrocarbon is within the above-mentioned range, compound (F) can be stabilized without lowering the purity of compound (F). A more excessive amount of aliphatic hydrocarbon may lower the purity of compound (F), and may impair the physical property of a polymer obtained by polymerizing compound (F).

Storage temperature is not more than a temperature at which aliphatic hydrocarbon is compatible with compound (F), and is generally less than the boiling point of aliphatic hydrocarbon, specifically not less than −50° C. and not more than 50° C. In addition, the storage pressure is preferably an atmospheric pressure or under pressurization. The storage atmosphere may be air atmosphere or inert gas (nitrogen gas, argon gas) atmosphere. Storage is generally performed in a sealed container in a shaded state.

Specific examples of the first storing method include an embodiment including mixing compound (F) and aliphatic hydrocarbon such that compound (F) and aliphatic hydrocarbon at more than 0 and not more than 50000 ppm are contained, and an embodiment including performing the thermal decomposition reaction in the production method of the present invention in the aforementioned state containing saturated aliphatic hydrocarbon and in a reactive distillation system to include compound (F) and the aliphatic hydrocarbon in the fraction generated by the thermal decomposition reaction.

In the first storing method, a polymerization inhibitor may be further contained. Specific examples of the polymerization inhibitor include 2,2,6,6-tetramethylpiperidine1-oxyl, p-benzoquinone, hydroquinone, methoquinine, 2,6-di-tert-butyl-4-methylphenol (BHT), 4-tert-butylcatechol, tert-butylhydroquinone, 2,5-di-tert-butylhydroquinone, 1,2,4-trihydroxybenzene, leucoquinizarine, chloranil, phenothiazine, Q-1300, Q-1301, tetraethylthiuram disulfide, sulfur and the like. A polymerization inhibitor may be used alone, or two or more kinds thereof may be used in combination.

As the second method for storing compound (F), an embodiment including retaining compound (F) obtained by the production method of the present invention at pH 6.5 or below can be mentioned. That is, when compound (F) is maintained at pH 6.5 or below, compound (F) can be stably stored for a long term.

Maintaining compound (F) at pH 6.5 or below means that, when 10 g of compound (F) and 10 g of $H_2O$ are suspended for 30 minutes under an air atmosphere at 25° C., then the suspension is partitioned by standing still and aqueous layer recovered, and pH of the aqueous layer is measured, the pH is 6.5 or below. The pH of the aqueous layer is measured using a pH meter.

The pH is preferably 1-5.0, particularly preferably 1-4.0. When pH is within the above-mentioned range, spontaneous polymerization of compound (F), which is α-fluoroacrylate ester, is easily suppressed.

The means for maintaining pH includes, for example, a method for containing inorganic acid in compound (F). The inorganic acid is not particularly limited as long as it is compatible with compound (F) to the extent that the pH is maintained. The inorganic acid may be any of a liquid inorganic acid, a solid inorganic acid and a gas inorganic acid at 25° C. To homogeneously stabilize compound (F), a liquid inorganic acid or gaseous inorganic acid is preferable, and a gaseous inorganic acid is more preferable. As the inorganic acid, hydrogen halide, sulfuric acid or nitric acid is preferable, hydrogen halide is more preferable, and one or more kinds of hydrogen halides selected from hydrofluoric acid and hydrogen chloride are particularly preferable.

Specific examples of the second storing method include an embodiment including introducing gaseous inorganic acid into compound (F) and dissolving as necessary to maintain compound (F) at pH 6.5 or below, and an embodiment including containing an inorganic acid represented by the formula HX (hydrogen halide) (wherein the definition and preferable range of X are as mentioned above), which can be by-produced in a thermal decomposition reaction in the production method of the present invention, in compound (F) without separation.

The storage temperature in the second storing method is not more than a temperature at which inorganic acid is compatible with compound (F) to the extent that the pH is maintained, and specifically not less than −50° C. and not more than 50° C. In addition, the storage pressure is preferably an atmospheric pressure or under pressurization. The storage atmosphere may be air atmosphere or inert gas (nitrogen gas, argon gas) atmosphere. The second storing method is generally performed in a sealed container in a shaded state.

Another embodiment of the second method for storing compound (F) is an embodiment for retaining compound (F) in a state containing hydrogen halide at more than 0 ppm and not more than 10000 ppm relative to compound (F). That is, compound (F) can be stably stored for a long term in a state of a composition containing compound (F) and hydrogen halide wherein the hydrogen halide is contained at more than 0 ppm and not more than 10000 ppm, relative to compound (F). As a preferable embodiment of such composition, a composition containing the composition (F) of the present invention and hydrogen halide, wherein the hydrogen halide is contained at more than 0 ppm and not more than 10000 ppm, relative to compound (F) can be mentioned.

Maintaining the state means that, when 10 g of compound (F) and 10 g of $H_2O$ are suspended for 30 minutes under an air atmosphere at 25° C., then the suspension is partitioned by standing still and aqueous layer is recovered, and the halogen ion content of the aqueous layer is measured as a hydrogen halide content, the halogen ion content is more than 0 ppm and not more than 10000 ppm. In this case, the pH of the aqueous layer is preferably not more than 6.5. The halogen ion content of the aqueous layer is measured using an ion meter, and the pH of the aqueous layer is measured using a pH meter.

The content of the hydrogen halide is preferably from more than 0 to 6000 ppm, more preferably from more than 0 to 2000 ppm.

When two or more kinds of hydrogen halides are used, the total thereof is appropriately adjusted so as to fall within the above-mentioned range. When the hydrogen halide is hydrogen chloride, the content of the hydrogen chloride is preferably from more than 0 to 5000 ppm, more preferably from more than 0 to 2000 ppm. When the hydrogen halide is hydrofluoric acid, the content of the hydrofluoric acid is preferably from more than 0 to 1000 ppm, more preferably from more than 0 to 500 ppm. When the content of hydrogen halide is within the above-mentioned range, spontaneous time-course polymerization of compound (F), which is α-fluoroacrylate ester, is easily suppressed.

Hydrogen halide is not particularly limited as long as it is compatible with compound (F) to the extent that the content thereof is retained. Hydrogen halide is preferably hydrogen chloride or hydrofluoric acid.

Specific examples of another second storing method include an embodiment including introducing one or more kinds of hydrogen halides selected from hydrogen chloride and hydrofluoric acid into compound (F) and dissolving as necessary to maintain the one or more kinds of hydrogen halides at more than 0 ppm and not more than 10000 ppm relative to component (F), and an embodiment including containing an inorganic acid represented by the formula HX (hydrogen halide) (wherein the definition and preferable range of X are as mentioned above), which can be by-produced in a thermal decomposition reaction in the production method of the present invention, in compound (F) without separation.

The storage temperature in another embodiment of the second storing method only needs to be a temperature at which inorganic acid is compatible with compound (F) to the extent that the state is retained, and generally not less than −50° C. and not more than 50° C. The storage pressure is preferably an atmospheric pressure or under pressurization. The storage atmosphere may be air atmosphere or inert gas (nitrogen gas, argon gas etc.) atmosphere. Generally, another embodiment of the second storing method is performed in a sealed container in a shaded state.

EXAMPLES

While the present invention is specifically explained in the following by way of Examples, the present invention is not limited by these examples. Analysis by gas chromatography method is also indicated as GC analysis and an area percentage value of the detection peak of each compound in GC analysis is indicated as mol %.

Compound ($A^1$), compound ($F^1$), compound ($P^1$) and compound ($Q^1$) are respectively compounds represented by the following formulas. A wavy line in the formulas shows that a steric configuration relating to a double bond of the fluorine atom may be E or Z.

The content of compound ($A^1$) was determined using $^1$H-NMR according to an internal standard method.

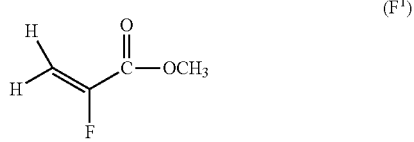

(F$^1$)

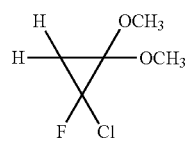

(A$^1$)

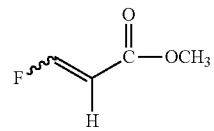

(P$^1$)

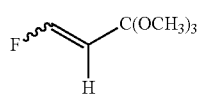

(Q$^1$)

For evaluation of the storage stability of compound ($F^1$), using gas chromatography analytical values (area percentage values), the relative area value of compound ($F^1$) was calculated with the area value of the internal standard substance as 1, and (relative area value after evaluation)÷(relative area value before evaluation) of compound ($F^1$) was calculated as a residual ratio and evaluated.

In addition, the pH and ion content of compound ($F^1$) in the evaluation of storage stability of compound ($F^1$) were measured by the following methods.

[Method for Measuring pH]

In an air atmosphere at 25° C., a preparation product (10 g) and $H_2O$ (10 g) were mixed and suspended for 30 min. Then, the suspension was partitioned by standing, the aqueous layer was recovered, and the pH of the aqueous layer was measured by a pH meter (manufactured by SATO KEIRYOKI MFG. CO., LTD., model number SK-620PH). For the measurement, phthalic acid salt (pH 4) was used as an indicator, a sensor probe of the pH meter was immersed in a measurement sample by not less than 3 cm and the measurement was performed.

[Method for Measuring Ion Content]

An ion meter (manufactured by HORIBA, Ltd. model number F-53) was used, an ion-selective electrode (8002 type) was used as an electrode, and a phenolphthalein solution was used as an indicator. A preparation product was added to a polyethylene bottle, an appropriate amount of distilled water was added, then, a phenol phthalein solution was added, and a 0.1N aqueous sodium hydroxide solution was added until the inner solution reached neutral (pH=7-8). The standard solution (potassium chloride solution) was placed in the electrode, the measurement value was read, the measurement results were converted to concentration and the halogen ion concentration of the sample was measured.

[Example 1] Production Example of Composition Containing Compound ($A^1$)

In a flask (inner volume 300 mL) were mixed $CH_2$=$C(OCH_3)_2$ (20 g), tetrabutylammonium bromide (0.1 g), 48% aqueous potassium hydroxide solution (80 g) and hexane (40 g), and the mixture was cooled to 5° C. and stirred. While maintaining the inner temperature of the flask at less than 10° C., $CHCl_2F$ (32 g) was continuously fed. After completion of the feeding, the solution in the flask was subjected to GC analysis to confirm the disappearance of $CH_2$=$C(OCH_3)_2$. Then, distilled water (40 g) was poured into the flask and the mixture was stirred and then allowed to stand to recover the organic layer as a composition containing compound ($A^1$).

The content of compound ($A^1$) in the organic layer was 29 g (yield 83.6%), and the organic layer contained 18 mol % of compound ($A^1$), 0.054 mol % of compound ($P^1$) and 0.108 mol % of compound ($Q^1$).

[Example 2] Production Example of Purified Product Containing Compound ($A^1$)

<Distillation Step>

The composition obtained in Example 1 was evaporated under reduced pressure using a distillation column with 20 theoretical stages under the conditions of reflux ratio 15:1, pressure 11.3 Torr, pot inner temperature 35° C. to give a colorless liquid distillate. The distillate had a compound ($A^1$) content of 27 g and contained 95.4 mol % of compound ($A^1$), 0.36 mol % of compound ($P^1$) and 0.72 mol % of compound ($Q^1$).

<Washing Step>

An aqueous solution (5.4 g) of 10 mass % potassium hydroxide was charged in a flask, and the inner temperature was consistently maintained at 20° C. with stirring. The distillate (28 g) was charged in the flask and maintained with stirring. Then, the flask was stood to allow for separation of the inner solution into two layers, and the organic layer (27 g) was recovered as a compound ($A^1$)-containing purified product. The organic layer had a compound ($A^1$) content of 27 g, and contained 99.3 mol % of compound ($A^1$), 0.01 mol % of compound ($P^1$) and 0.02 mol % of compound ($Q^1$). The organic layer contained a trace amount of hexane.

[Examples 3-5] Production Examples of Compound ($A^1$)-Containing Purified Product Using a composition obtained in the same manner as in Example 1, a purification treatment was performed in the same manner as in Example 2 except that the pot temperature in the distillation step was changed in Example 3, and the concentration of the aqueous potassium hydroxide solution in the washing step was changed in Example 4. In Example 5 as a comparative example, the order of processes was changed and the purification treatment contained a washing step and a distillation step in this order. The respective conditions and the composition of the obtained compound ($A^1$)-containing purified products are collectively shown in the following Table 1.

jected to a purification treatment in the order of washing step and distillation step, a composition of highly-pure compound ($A^1$) can be obtained by a purification treatment in the order of the former.

[Example 6] Production Example of Compound ($F^1$)-Containing Composition

In a three-necked flask (inner volume 100 mL) connected to a receiver cooled to 0° C. (initially added with 0.5 g of 2,6-di-tert-butyl-4-methylphenol as polymerization inhibitor (hereinafter to be also indicated as BHT)) were charged BHT (0.5 g) and 1,2,4-trichlorobenzene (100 mL). The inner pressure of 360 Torr and the inner temperature at 145° C. were maintained, and dropwise addition of purified product (20 g) of Example 2 was started to perform the thermal decomposition reaction of compound ($A^1$) and the generated fraction was collected in the receiver to give compound ($F^1$).

The content of compound ($F^1$) in the fraction was 12.3 g, and the fraction (compound ($F^1$)-containing composition) contained 99.3 mol % of compound ($F^1$), 0.01 mol % of compound ($P^1$), and 0.02 mol % of compound ($Q^1$). The fraction contained a trace amount of hexane.

[Example 7] Production Example (Comparative Example) of Compound ($F^1$)-Containing Purified Product In the same manner as in Example 6 except that the purified product to be added dropwise was changed to the purified product obtained in Example 5, a thermal decomposition reaction was performed to give a fraction. The respective fraction compositions are shown in the following Table 2.

TABLE 2

| Ex. | Purified product used | Composition of fraction | | | ratio*3 [mol %] | compound ($F^1$) yield*4 [mol %] |
| | | compound ($F^1$) [mol %] | compound ($P^1$) [mol %] | compound ($Q^1$) [mol %] | | |
| --- | --- | --- | --- | --- | --- | --- |
| 6 | Example 2 | 99.3 | 0.01 | 0.02 | 0.03 | 96 |
| 7 | Example 5 | 98.5 | 0.22 | 0.11 | 0.34 | 95 |

*3 shows ratio of total content of compound ($P^1$) and compound ($Q^1$) relative to the content of compound ($F^1$).
*4 The amount (content standard) of compound ($A^1$) contained in the purified product used was taken as the standard.

TABLE 1

| Ex. | Distillation step pot inner temperature [° C.] | Washing step KOH concentration [wt %] | Composition of purified product | | | ratio*1 [mol %] | compound ($A^1$) yield*2 [mol %] |
| | | | compound ($A^1$) [mol %] | compound ($P^1$) [mol %] | compound ($Q^1$) [mol %] | | |
| --- | --- | --- | --- | --- | --- | --- | --- |
| 2 | 35 | 10 | 99.3 | 0.01 | 0.02 | 0.03 | 83 |
| 3 | 75 | 10 | 98.4 | 0.23 | 0.57 | 0.81 | 77 |
| 4 | 35 | 45 | 98.2 | 0.24 | 0.25 | 0.50 | 83 |
| 5 | 35 | 10 | 97.6 | 0.37 | 0.64 | 1.03 | 83 |

*1 shows ratio of total content of compound ($P^1$) and compound ($Q^1$) to the content of compound ($A^1$).
*2 was calculated from the content of compound ($A^1$) based on the amount of starting material $CH_2$=$C(OCH_3)_2$ as the standard.

As is clear from the composition of purified product of Example 2 subjected to a purification treatment in the order of distillation step and washing step, and the composition of purified product of Example 5 (comparative example) sub- As is clear from the results of Example 6 (purified product of Example 2 was used) and Example 7 (purified product of Example 5, which is comparative example, was used), a composition of highly-pure compound ($F^1$) was obtained when a compound ($A^1$)-containing purified product obtained by a purification treatment in the order of distillation step and washing step was used.

[Example 8] Storage Evaluation Example (First Storing Method) of Compound ($F^1$)

Compound ($F^1$) (reagent manufactured by Wako Pure Chemical Industries, Ltd.) was subjected to single distillation to give compound ($F^1$) free of a polymerization inhibitor, 2,2,6,6-tetramethylpiperidine1-oxyl (hereinafter to be also indicated as single distillation product). The single distillation product was analyzed, and aliphatic hydrocarbon was not detected.

Hexane was added to the single distillation product, and samples 1, 2, 3 respectively containing 100 ppm, 1000 ppm, 10000 ppm of hexane relative to compound ($F^1$) were prepared. In addition, the compound ($F^1$)-containing composition obtained in Example 6 contained 1000 ppm of hexane relative to compound ($F^1$).

In an air atmosphere, an internal standard substance (trifluoroethanol 100 ppm) was added to each of the samples, stored in a sealed and shaded state at 0° C. for 3 days, and the stability of compound ($F^1$) was evaluated. The results are shown in Table 3.

TABLE 3

| Sample | Composition hexane content [ppm] | Residual ratio [%] |
|---|---|---|
| single distillation product | 0 | 90.5 |
| sample 1 | 100 | 92.1 |
| sample 2 | 1000 | 93.4 |
| sample 3 | 10000 | 97.6 |
| composition of Example 6 | 1000 | 95.5 |

[Example 9] Storage Evaluation Example (Second Storing Method) of Compound ($F^1$)

The single distillation product had pH 7.0, and neither hydrogen chloride nor hydrofluoric acid was detected.

A hydrogen chloride gas was blown into the single distillation product, and sample 4 with pH 3, which is hydrogen chloride-containing compound ($F^1$) and contains 100 ppm of chloride ion relative to compound ($F^1$), was obtained. In the same manner, sample 5 with pH 2, which is hydrogen chloride-containing compound ($F^1$) and contains 1200 ppm of chloride ion relative to compound ($F^1$), was obtained.

Then, a hydrofluoric acid gas was blown into compound ($F^1$) and sample 6 with pH 3, which is hydrofluoric acid-containing compound ($F^1$) and contains 20 ppm of fluoride ion relative to compound ($F^1$), and sample 7 with pH 2, which is hydrofluoric acid-containing compound ($F^1$) and contains 500 ppm of fluoride ion relative to compound ($F^1$), were obtained. Furthermore, hydrogen chloride gas and hydrofluoric acid gas were successively blown into compound ($F^1$), and sample 8 with pH 1, which is compound ($F^1$) containing hydrogen chloride and hydrofluoric acid and contains 1200 ppm of chloride ion and 20 ppm of fluoride ion each relative to compound ($F^1$), was obtained.

In addition, the compound ($F^1$)-containing composition obtained in Example 6 was confirmed to contain hydrogen chloride and hydrofluoric acid, contain 800 ppm of chloride ion and 20 ppm of fluoride ion each relative to compound ($F^1$) and have pH 1.

In an air atmosphere, an internal standard substance (trifluoroethanol 100 ppm) was added to each of the samples, stored in a sealed and shaded state at 25° C. for 3 days, and the stability of compound ($F^1$) was evaluated. The results are shown in Table 4.

TABLE 4

| | | Composition of fraction | | |
|---|---|---|---|---|
| Sample | pH | HCL concentration [ppm] | HF concentration [ppm] | Residual ratio [%] |
| single distillation product | 7.0 | 0 | 0 | 85.4 |
| sample 4 | 3 | 100 | 0 | 97.2 |
| sample 5 | 2 | 1200 | 0 | 98.1 |
| sample 6 | 3 | 0 | 20 | 97.4 |
| sample 7 | 2 | 0 | 500 | 98.7 |
| sample 8 | 1 | 1200 | 20 | 99.3 |
| composition of Example 6 | 1 | 800 | 20 | 99.0 |

[Example 10] Production Example of Polymer

A composition containing compound ($F^1$)-containing composition (21.6 g) of Example 6, 1,7-octadiene (1.2 g) and divinylbenzene (1.2 g), and an aqueous solution of sodium chloride (4.2 g), poly(vinyl alcohol) (1.2 g), disodium hydrogen phosphate heptahydrate (1.0 g), disodium hydrogen phosphate monohydrate (0.08 g), sodium nitrite (0.02 g), water (101.5 g) and lauroyl peroxide were charged and mixed in a reactor, and the reactor inner temperature was maintained at 30° C. While stirring the inside of the reactor, the inner temperature was continuously raised to 95° C., and the composition was polymerized. After polymerization, the solution in the reactor was cooled and the organic phase was recovered. Under stirring, water was added to the organic phase, and the generated solid was recovered and further washed with water to give a crosslinked polymer (15 g), which is a copolymer of compound ($F^1$), 1,7-octadiene and divinylbenzene.

INDUSTRIAL APPLICABILITY

According to the present invention, a production method of highly-pure α-fluoroacrylate ester is provided. According to the present invention, moreover, a composition containing a highly-pure fluorocyclopropane derivative preferably used for the production of α-fluoroacrylate ester, and a composition containing highly-pure α-fluoroacrylate ester preferably used as a monomer for various polymers are provided. Furthermore, according to the present invention, a method for storing α-fluoroacrylate ester stably for a long term is provided.

This application is based on patent application Nos. 2016-059110, 2016-059111 and 2016-059112 filed in Japan, the contents of which are incorporated in full herein.

The invention claimed is:
1. A method of producing a compound represented by formula (F), the method comprising:
purifying a composition comprising a compound represented by formula (A) by distillation and then washing with an aqueous alkali solution to give a purified product comprising the compound represented by formula (A), and thermally decomposing the purified product to give the compound represented by formula (F), wherein the compound (A) and the compound (F) are as follows:

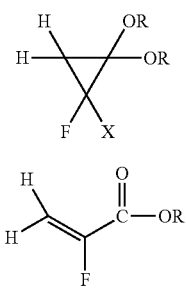
(A)

(F)

wherein each R is independently a monovalent hydrocarbon group, and

X is a halogen atom.

2. The method according to claim 1, the method further comprises:

reacting a compound represented by formula CH$_2$=C(OR)$_2$ and a compound represented by formula CHClFX in the presence of an alkali metal hydroxide, thereby obtaining the composition comprising the compound represented by formula (A).

3. The method according to claim 1, wherein the distillation comprises evaporating under reduced pressure at 70° C. or lower.

4. The method according to claim 1, wherein an alkali concentration of the aqueous alkali solution is maintained at 40 mass % or less in the washing.

5. The method of claim 1, wherein compound (F) is directly obtained by thermally decomposing the compound of formula (A) in the purified product.

6. The method according to claim 2, wherein the composition further comprises one or more of a compound of formula (P) and a compound of formula (Q)

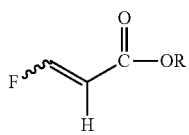
(P)

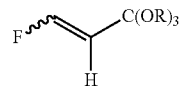
(Q)

wherein each R is independently a monovalent hydrocarbon group.

7. The method according to claim 6, wherein the purified product contains a ratio of total moles of the compounds of formula (P) and formula (Q) to the moles of compound (A) that is lower relative to a ratio of total moles of the compounds of formula (P) and formula (Q) to the moles of compound (A) in the composition.

8. The method according to claim 1, wherein the distillation is carried out with a distillation column having a plurality of theoretical stages.

9. The method according to claim 8, wherein the distillation is carried out at a pressure of 11.3 Torr or lower.

10. The method of claim 1, wherein the distillation is carried out under reduced pressure at a temperature of not more than 50° C.

11. The method according to claim 1, wherein compound (A) and compound (F) have the following formulas (A1) and (F1), respectively:

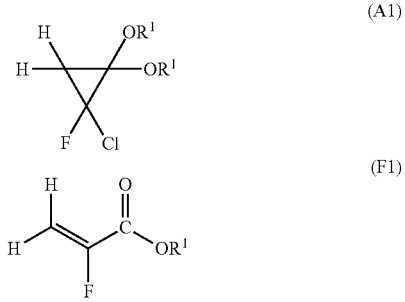
(A1)

(F1)

wherein R$^1$ is independently selected from the group consisting of a methyl group, an ethyl group, an n-propyl group, an iso-propyl group, an n-butyl group, an iso-butyl group and a tert-butyl group.

12. The method according to claim 11, wherein the washing is carried out with an aqueous KOH solution having a KOH concentration of 10 wt % or less.

13. The method according to claim 6, wherein after the purifying, a ratio of total mols of the compounds of the formula (P) and the formula (Q) to the mols of compound (A) is 0.50 mol % or less.

* * * * *